United States Patent
Shafer et al.

(10) Patent No.: US 11,918,422 B2
(45) Date of Patent: Mar. 5, 2024

(54) SYSTEMS AND METHODS FOR COMMUNICATING OVER A REDUCED NUMBER OF CONDUCTORS IN A TELEOPERATIONAL SYSTEM

(71) Applicant: INTUITIVE SURGICAL OPERATIONS, INC., Sunnyvale, CA (US)

(72) Inventors: David C. Shafer, Menlo Park, CA (US); John A Barton, Mountain View, CA (US)

(73) Assignee: Intuitive Surgical Operation, Inc., Sunnyvale, CA (US)

( * ) Notice: Subject to any disclaimer, the term of this patent is extended or adjusted under 35 U.S.C. 154(b) by 480 days.

(21) Appl. No.: 16/954,783

(22) PCT Filed: Dec. 17, 2018

(86) PCT No.: PCT/US2018/065989
§ 371 (c)(1),
(2) Date: Jun. 17, 2020

(87) PCT Pub. No.: WO2019/126028
PCT Pub. Date: Jun. 27, 2019

(65) Prior Publication Data
US 2021/0007826 A1    Jan. 14, 2021

Related U.S. Application Data

(60) Provisional application No. 62/607,634, filed on Dec. 19, 2017.

(51) Int. Cl.
| | |
|---|---|
| *A61B 1/00* | (2006.01) |
| *A61B 1/05* | (2006.01) |
| *A61B 34/00* | (2016.01) |
| *A61B 34/37* | (2016.01) |
| *A61B 90/00* | (2016.01) |

(52) U.S. Cl.
CPC ........ *A61B 90/361* (2016.02); *A61B 1/00018* (2013.01); *A61B 1/00027* (2013.01);
(Continued)

(58) Field of Classification Search
CPC ....... A61B 90/361; A61B 90/36; A61B 90/37; A61B 34/70–71; A61B 34/74;
(Continued)

(56) References Cited

U.S. PATENT DOCUMENTS

| | | | | |
|---|---|---|---|---|
| 2011/0001851 | A1* | 1/2011 | Nakamura | A61B 1/00009 348/241 |
| 2012/0016202 | A1* | 1/2012 | Baum | A61B 1/00114 600/182 |

(Continued)

FOREIGN PATENT DOCUMENTS

| | | |
|---|---|---|
| WO | WO-2014145248 A1 | 9/2014 |
| WO | WO-2016106114 A1 | 6/2016 |
| WO | WO-2017160564 A2 | 9/2017 |

OTHER PUBLICATIONS

International Preliminary Report on Patentability for Application No. PCT/US2018/065989, dated Jul. 2, 2020, 6 pages.

(Continued)

*Primary Examiner* — Ryan N Henderson
*Assistant Examiner* — Pamela F Wu
(74) *Attorney, Agent, or Firm* — Haynes & Boone, LLP

(57) ABSTRACT

A system and method for a teleoperational medical system is provided is provided that can include one or more processors, conductors can extend through a shaft with an interface positioned at a proximal end of the shaft and a sensor(s) positioned at a distal end of the shaft, and the conductors can electrically couple the sensor(s) to the processor via the interface. Signals can be transmitted over the conductors between the sensor(s) and the processor(s). The signals can include power and control signals transmitted in one direction over the conductors and sensor data transmitted in an opposite direction over the same conductors.

20 Claims, 8 Drawing Sheets

(52) U.S. Cl.
CPC ............... *A61B 1/05* (2013.01); *A61B 34/37* (2016.02); *A61B 34/74* (2016.02); *A61B 1/00149* (2013.01); *A61B 1/0016* (2013.01); *A61B 1/00183* (2013.01)

(58) Field of Classification Search
CPC ............ A61B 1/00011; A61B 1/00018; A61B 1/00025; A61B 1/00027; A61B 1/00032; A61B 1/00096; A61B 1/00114; A61B 1/04; A61B 1/045; A61B 1/05
USPC ......................................................... 600/424
See application file for complete search history.

(56) References Cited

U.S. PATENT DOCUMENTS

| | | | | |
|---|---|---|---|---|
| 2012/0310043 | A1* | 12/2012 | Hu | .......................... A61B 1/051 600/109 |
| 2014/0135579 | A1* | 5/2014 | Brichard | ............ A61B 1/00018 600/117 |
| 2015/0265143 | A1 | 9/2015 | Yoon | |
| 2016/0072989 | A1* | 3/2016 | Kennedy, II | ........... A61B 1/051 348/76 |
| 2016/0310077 | A1* | 10/2016 | Hunter | ..................... A61C 8/00 |
| 2017/0095667 | A1* | 4/2017 | Yakovlev | .............. A61B 5/1118 |
| 2018/0151272 | A1* | 5/2018 | Watanabe | .......... A61B 1/00114 |

OTHER PUBLICATIONS

International Search Report and Written Opinion for Application No. PCT/US2018/065989, dated Apr. 10, 2019, 9 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

SYSTEMS AND METHODS FOR COMMUNICATING OVER A REDUCED NUMBER OF CONDUCTORS IN A TELEOPERATIONAL SYSTEM

CROSS-REFERENCE TO RELATED APPLICATIONS

This patent application is the U.S. national phase of International Application No. PCT/US2018/065989, filed Dec. 17, 2018, which designated the U.S. and claims priority to and the benefit of the filing date of U.S. Provisional Application No. 62/607,634, filed Dec. 19, 2017, all of which are incorporated by reference in their entirety.

FIELD

The present disclosure is directed to systems and methods for imaging sensors in an imaging system of a teleoperational system over a reduced number of conductors and more particularly to systems and methods for powering, controlling, and receiving data from imaging sensors that image a patient's anatomy during a teleoperational medical procedure.

BACKGROUND

Minimally invasive medical techniques are intended to reduce the amount of tissue that is damaged during invasive medical procedures, thereby reducing patient recovery time, discomfort, and harmful side effects. Such minimally invasive techniques may be performed through natural orifices in a patient anatomy or through one or more surgical incisions. Through these natural orifices or incisions, clinicians may insert medical tools to reach a target tissue location. These tools may be inserted through cannulas that are inserted into the natural orifices or incisions prior to inserting the medical tools into the patient anatomy. Minimally invasive medical tools include instruments such as therapeutic instruments, diagnostic instruments, and surgical instruments. Minimally invasive medical tools may also include imaging instruments such as endoscopic instruments. Imaging instruments provide a user with a field of view within the patient anatomy. Some minimally invasive medical tools and imaging instruments may be teleoperated or otherwise computer-assisted.

Various minimally invasive medical tools (e.g. flexible imaging instruments such as endoscopes) can require transmission of high-speed data, control signals and power from/ to the instrument tip, while undergoing repeated cycles of flexing over sharp angles within a small space. The useful life of a flexible imaging instrument can be limited by the electrical connections inside flexible joints. In existing imaging instruments, dedicated wiring may be required for each of the three types of interface connections needed for power, control signals, and high speed digital data (such as video data). All of this wiring must pass through a narrow shaft and terminate to a small tip of the flexible part of the imaging instrument. When a cable with wire members having a different stiffness (such as shielded pairs for high-speed data, and individual wires for control signals and power) are flexed in a small space, asymmetric forces on the cable members tend to push the members axially, which can cause bunching and thereby limit the life of the tool. Improved interconnects suited for use with minimally invasive medical tools is needed.

SUMMARY

The embodiments of the invention are summarized by the claims that follow the description.

In one embodiment, an imaging system for imaging an anatomy of a patient can include a processor, an interface, at least one imaging sensor, first and second conductors, a shaft with the interface positioned at a proximal end of the shaft and the imaging sensor positioned at a distal end of the shaft, wherein the first and second conductors can extend though the shaft and electrically couple the imaging sensors to the processor via the interface, with signals and power transmitted over the first and second conductors between the imaging sensor and the processor.

The first and second conductors can be helically twisted about each other along a length of the first and second conductors. Also, the first conductor can be coaxially positioned within a first shield material forming a first coax cable, and the second conductor can be coaxially positioned within a second shield material forming a second coax cable. The first and second shield materials can be electrically grounded. The ground can be a local ground reference, not necessarily connected to earth ground.

A third shield material can at least partially surround the first and second conductors along a length of the first and second conductors, forming a shielded twisted pair cable. The power can be a DC voltage that powers the imaging sensor. The signals can also include low-speed control signals transmitted from the interface to the imaging sensor at a low-frequency spectrum and high-speed sensor data signals transmitted from the imaging sensor to the interface at a high-frequency spectrum. The low-speed control signals can be encoded and shaped to occupy a low frequency band in a range of 3 Mbps to 15 Mbps, and the high-speed sensor data signals can be encoded and shaped to occupy a high frequency band in a range of 100 MHz to 6.25 GHz.

The low-speed control signals can be transmitted from the interface during a first allocated time period, and high-speed sensor data signals are transmitted from the imaging sensor at a high-frequency during a second allocated time period. The first allocated time period may not overlap the second allocated time period.

The first and second conductors form a communication lane that transmits the signals and power between the imaging sensor and the processor, and the system can include multiple communication lanes.

In one embodiment, a teleoperational medical system is provided that can include a control system with one or more processors, a teleoperational manipulator arm, and an imaging system attached to the teleoperational manipulator arm. The imaging system can include imaging sensors that detect image data and transmit imaging sensor data signals to the control system, a camera interface that interfaces the imaging sensors to the control system, first and second conductors that electrically couple the control system to the imaging sensors via the camera interface, a rigid elongate member with the imaging sensors positioned at a distal end of the rigid elongate member, and the camera interface positioned at a proximal end of the rigid elongate member, with the first and second conductors positioned within the rigid elongate member. The control and power signals can be transmitted from the control system to the imaging sensors via the camera interface and the first and second conductors, and the imaging sensor data signals can be transmitted from the imaging sensors to the control system via the camera interface and the first and second conductors.

The power signals supply power to the imaging sensors. The power signals can include a first voltage carried to the imaging sensors by the first conductor and a second voltage carried to the imaging sensors by the second conductor.

The control signals can be encoded and shaped to occupy a low frequency spectrum, and the imaging sensor data signals can be encoded and shaped to occupy a high frequency spectrum. The power signals, control signals, and imaging sensor data signals can be transmitted simultaneously by the first and second conductors. The control signals and imaging sensor data signals can be transmitted by the first and second conductors at separate time periods.

The first and second conductors can be surrounded by one or more grounded shields, which can supply a ground reference to the imaging sensors.

In one embodiment, a method of imaging an anatomy of a patient is provided which can include a teleoperational manipulator arm of a teleoperational medical system with an elongate member attached. The elongate member can include a lumen, imaging sensors positioned at a distal end of the elongate member, a camera interface positioned at a proximal end of the elongate member, and first and second conductors positioned within the lumen, where the first and second conductors can electrically couple the imaging sensors to the camera interface.

The method can also include operations of transmitting a power signal to the imaging sensors via the first and second conductors thereby powering the imaging sensors, transmitting control signals to the imaging sensors from the camera interface via the first and second conductors, transmitting imaging sensor data signals to the camera interface from the imaging sensors via the first and second conductors, and receiving the imaging sensor data signals at the one or more controllers and displaying an image, based on the imaging sensor data signals, on a display device.

The method can also include operations of transmitting the control signals from the camera interface to the imaging sensors within a low-frequency spectrum while, at the same time, transmitting the imaging sensor data signals from the imaging sensors to the camera interface within a high-frequency spectrum.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

Figure 1A:
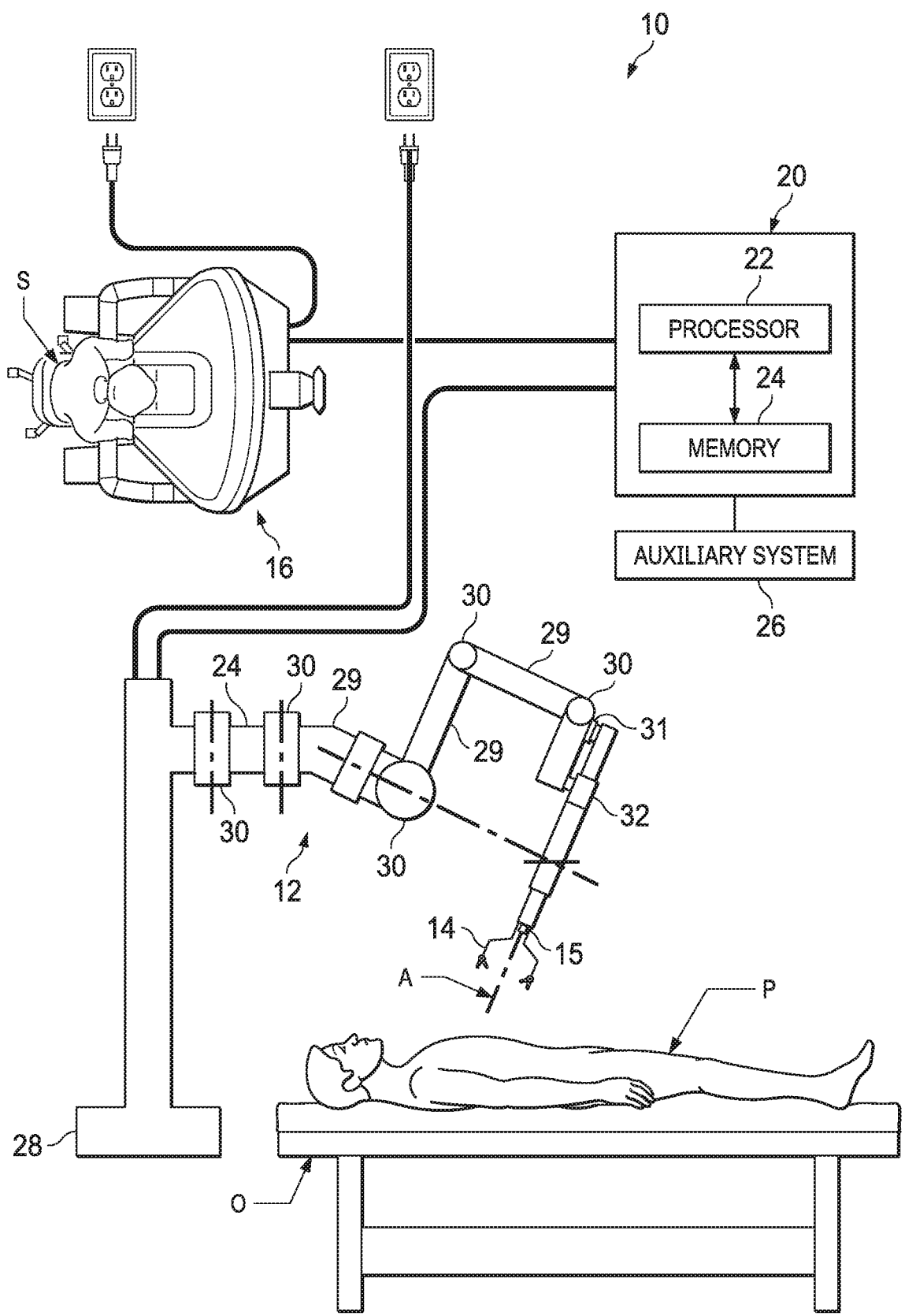
FIG. 1A is a schematic view of a teleoperational medical system, in accordance with an embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or operations described with respect to one embodiment may be combined with the features, components, and/or operations described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments.

For the sake of brevity, the numerous iterations of these combinations will not be described separately. For simplicity, in some instances the same reference numbers are used throughout the drawings to refer to the same or like parts.

Although some of the examples described herein often refer to surgical procedures or tools, or medical procedures or tools, the techniques disclosed also apply to non-medical procedures and non-medical tools. For example, the tools, systems, and methods described herein may be used for non-medical purposes including industrial uses, general robotic uses, and sensing or manipulation of non-tissue work pieces. Other example applications involve surgical or non-surgical cosmetic improvements, imaging of or gathering data from human or animal anatomy, training medical or non-medical personnel, performing procedures on tissue removed from human or animal anatomies (without return to a human or animal anatomy), and performing procedures on human or animal cadavers.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Referring to FIG. 1A of the drawings, a teleoperational medical system for use in, for example, medical procedures including diagnostic, therapeutic, or surgical procedures, is generally indicated by the reference numeral 10. As will be described, the teleoperational medical systems of this disclosure are under the teleoperational control of a surgeon. In alternative embodiments, a teleoperational medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures. As shown in FIG. 1A, the teleoperational medical system 10 generally includes a teleoperational assembly 12 mounted to or near an operating table O on which a patient P is positioned. The teleoperational assembly 12 may be referred to as a patient side cart. A medical instrument system 14 and an endoscopic imaging system 15 are operably coupled to the teleoperational assembly 12. An operator input system 16 allows a surgeon or other type of clinician S to view images of or representing the surgical site and to control the operation of the medical instrument system 14 and/or the endoscopic imaging system 15.

The operator input system 16 may be located at a surgeon's console, which is usually located in the same room as operating table O. It should be understood, however, that the surgeon S can be located in a different room or a completely different building from the patient P. In various embodiments, a teleoperational medical system may include more than one operator input system 16 and surgeon's console. In various embodiments, an operator input system may be available on a mobile communication device including a tablet or a laptop computer. Operator input system 16 generally includes one or more control device(s) for controlling the medical instrument system 14. The control device(s) may include one or more of any number of a variety of input devices, such as hand grips, joysticks, trackballs, data gloves, trigger-guns, foot pedals, hand-operated controllers, voice recognition devices, touch screens, body motion or presence sensors, and the like.

In some embodiments, the control device(s) will be provided with the same degrees of freedom as the medical instruments of the teleoperational assembly to provide the surgeon with telepresence, the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon with telepresence. In some embodiments, the control device(s) are manual input devices which move with six degrees of freedom, and which may also include an actuatable handle for actuating instruments (for example, for closing grasping jaw end effectors, applying an electrical potential to an electrode, delivering a medicinal treatment, and the like).

The teleoperational assembly 12 supports and manipulates the medical instrument system 14 while the surgeon S views the surgical site through the operator input system 16. An image of the surgical site can be obtained by the endoscopic imaging system 15, such as a stereoscopic endoscope, which can be manipulated by the teleoperational assembly 12 to orient the endoscope 15. A control system 20 can be used to process the images of the surgical site for subsequent display to the surgeon S through the operator input system 16 (can also be referred to as a surgeon's console 16). The number of medical instrument systems 14 used at one time will generally depend on the diagnostic or surgical procedure and the space constraints within the operating room among other factors. The teleoperational assembly 12 may include a kinematic structure of one or more non-servo controlled links (e.g., one or more links that may be manually positioned and locked in place, generally referred to as a set-up structure) and a teleoperational manipulator.

The teleoperational assembly 12 includes a plurality of motors that drive inputs on the medical instrument system 14. These motors move in response to commands from the control system (e.g., control system 20). The motors include drive systems which when coupled to the medical instrument system 14 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like. Instruments 14 may include end effectors having a single working member such as a scalpel, a blunt blade, an optical fiber, or an electrode. Other end effectors may include, for example, forceps, graspers, scissors, or clip appliers.

The teleoperated assembly 12 is mechanically supported by a base 28. Links 29 of the assembly 12 are coupled together and to the base 28 through joints 30. The joints 30 may be passive joints that allow manual positioning of the assembly 12 when their brakes are released or may be active joints driven my motors. A carriage 31 coupled to the most distal link 29 is coupled to a linear drive mechanism to extend or retract a cannula 32 along an insertion axis A. The instruments 14, 15 extend within the cannula 32 and may extend distally from the cannula.

Endoscopic imaging systems (e.g., system 15) may be provided in a variety of configurations including rigid or flexible endoscopes. Rigid endoscopes include a rigid tube which may house a relay lens system for transmitting an image from a distal end to a proximal end of the endoscope, or may contain an image sensor at the distal end with power and signals transmitted through the rigid shaft. Flexible endoscopes may transmit images from a distal end to a proximal end of the endoscope using one or more flexible optical fibers, or may also have an image sensor at the distal end with power and signals transmitted through the flexible shaft. Endoscopes of either rigid or flexible design with image sensors at the distal end are referred to as "chip on the tip" designs. Regardless of whether the shaft is rigid or flexible, the common feature of these designs is a distal digital sensor such as a one or more charge-coupled devices (CCD) or a complementary metal oxide semiconductor (CMOS) devices that store image data, and a communication path for transmitting power and signals through the endoscope shaft. Endoscopic imaging systems may provide two- or three-dimensional images to the viewer. Two-dimensional images may provide limited depth perception. Three-dimensional stereo endoscopic images may provide the viewer with more accurate depth perception. Stereo endoscopic instruments employ stereo cameras to capture stereo images of the patient anatomy. An endoscopic instrument may be a fully sterilizable assembly with the endoscope cable, handle and shaft all rigidly coupled and hermetically sealed, or may be of such a design that the sterilizing means can reach into the separate parts of the endoscope.

The teleoperational medical system 10 also includes a control system 20. The control system 20 includes at least one memory 24 and at least one processor 22, and typically a plurality of processors 22, for effecting control between the medical instrument system 14, the operator input system 16, and other auxiliary systems 26 which may include, for example, imaging systems, audio systems (including an intercom system), fluid delivery systems, display systems, mobile vision carts, illumination systems, steering control systems, irrigation systems, and/or suction systems. The control system 20 also includes programmed instructions (e.g., a computer-readable medium storing the instructions) to implement some or all of the methods described in accordance with aspects disclosed herein.

While control system 20 is shown as a single block in the simplified schematic of FIG. 1A, the system may include two or more data processing circuits with one portion of the processing optionally being performed on or adjacent the teleoperational assembly 12, another portion of the processing being performed at the operator input system 16, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 20 supports wireless communication protocols such as Bluetooth, IrDA, HomeRF, IEEE 802.11, DECT, and Wireless Telemetry.

In some embodiments, control system 20 may include one or more servo controllers that receive force and/or torque feedback from the medical instrument system 14. Responsive to the feedback, the servo controllers transmit signals to the operator input system 16. The servo controller(s) may also transmit signals instructing teleoperational assembly 12 to move the medical instrument system(s) 14 and/or endoscopic imaging system 15 which extend into an internal surgical site within the patient body via openings in the body. Any suitable conventional or specialized servo controller may be used. A servo controller may be separate from, or integrated with, teleoperational assembly 12. In some embodiments, the servo controller and teleoperational assembly are provided as part of a teleoperational arm cart positioned adjacent to the patient's body.

The control system 20 can be coupled with the endoscope 15 and can include a processor to process captured images for subsequent display, such as to a surgeon on the surgeon's console, or on another suitable display located locally and/or remotely. For example, where a stereoscopic endoscope is used, the control system 20 can process the captured images to present the surgeon with coordinated stereo images of the surgical site. Such coordination can include alignment between the opposing images and can include adjusting the stereo working distance of the stereoscopic endoscope.

In alternative embodiments, the teleoperational system may include more than one teleoperational assembly and/or more than one operator input system. The exact number of manipulator assemblies will depend on the surgical procedure and the space constraints within the operating room, among other factors. The operator input systems may be collocated, or they may be positioned in separate locations. Multiple operator input systems allow more than one operator to control one or more manipulator assemblies in various combinations.

Figure 1B:
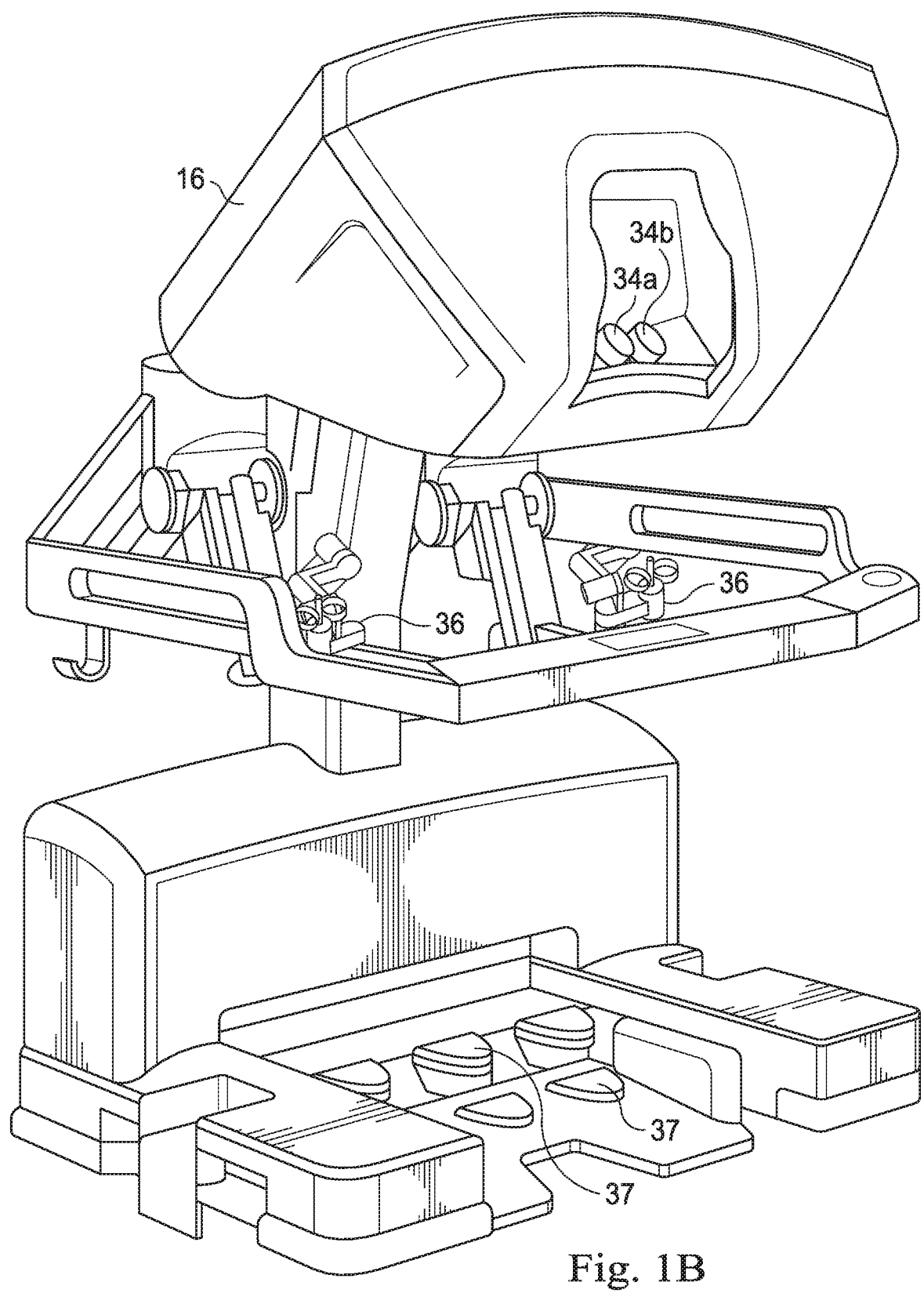
FIG. 1B is a representative perspective view of a surgeon's control console for a teleoperational medical system, in accordance with many embodiments.

FIG. 1B is a perspective view of the surgeon's console 16. The surgeon's console 16 includes a left eye display 34a and a right eye display 34b for presenting the surgeon S with a coordinated stereo view of the surgical environment that enables depth perception. The console 16 further includes one or more input control devices 36, which in turn cause the teleoperational assembly 12 to manipulate one or more instruments or the endoscopic imaging system. The input control devices 36 can provide the same degrees of freedom as their associated instruments 14 to provide the surgeon S with telepresence, or the perception that the input control devices 36 are integral with the instruments 14 so that the surgeon has a strong sense of directly controlling the instruments 14. To this end, position, force, and tactile feedback sensors (not shown) may be employed to transmit position, force, and tactile sensations from the instruments 14 back to the surgeon's hands through the input control devices 36. Input control devices 37 are foot pedals that receive input from a user's foot. Each of the surgical tools 14a, 14b, 14c may be associated with one of the control devices 36. The Surgeon performs a medical procedure by manipulating the control devices 36 so that the control system 20 causes corresponding movement of one of the associated surgical tools 14a, 14b, 14c while the Surgeon views the surgical site in 3-D on the eye displays 34a, 34b as it is captured by the imaging system 15. During the medical procedure, the surgical tools may be reassigned to a different one of the control devices 36.

Figure 1C:
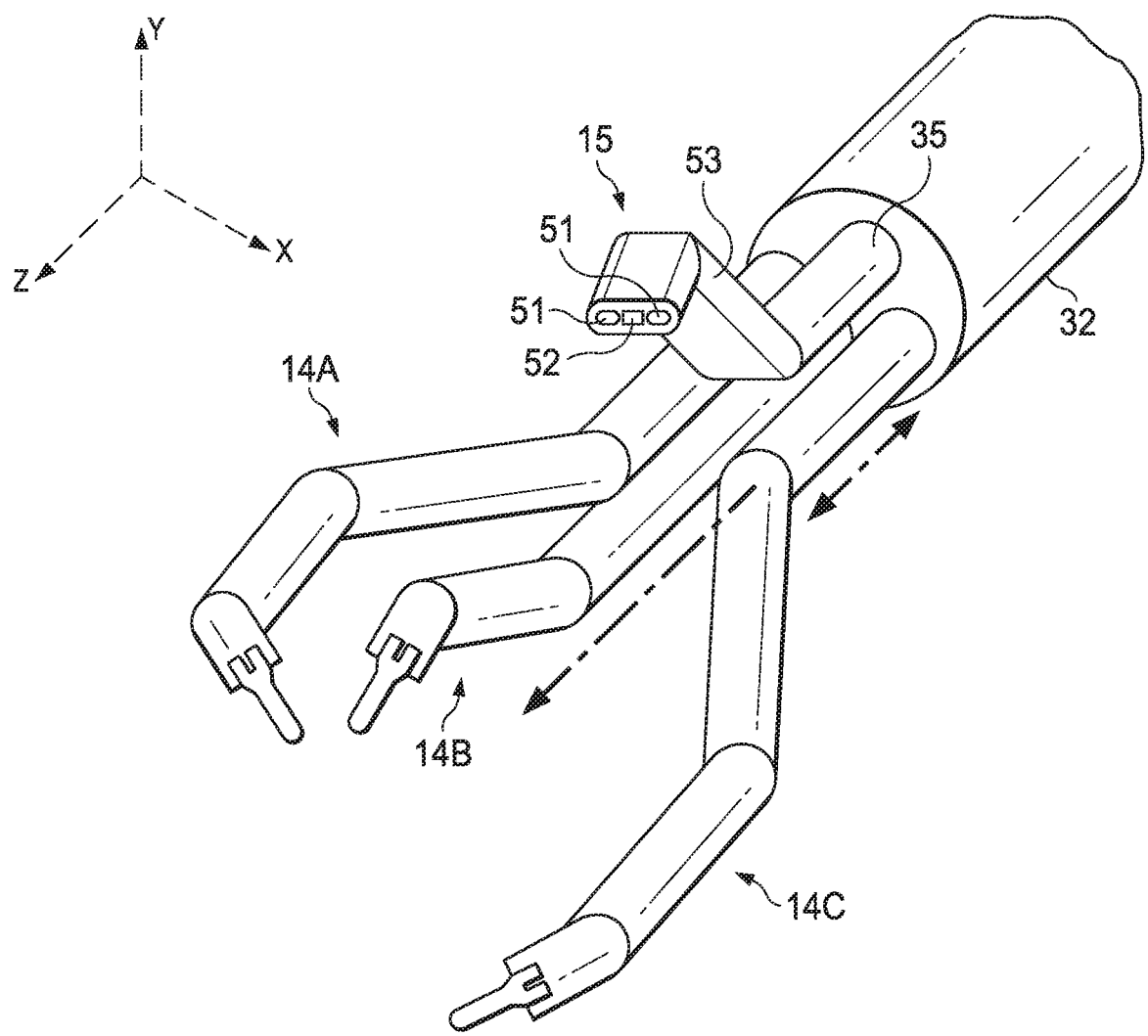
FIG. 1C is a perspective view of a distal end of a cannula, according to one example of principles described herein.

FIG. 1C is a perspective view of the distal end of the cannula 32. In some embodiments, the cannula 32 may be rigid. Alternatively, it may be formed of flexible material or comprise actively and/or passively bendable sections so that the cannula 32 may conform to the shapes of body lumens as it moves therethrough to a surgical site within a patient.

Three surgical tools 14a, 14b, 14c (e.g., instrument systems 14) and an imaging system 15 extend from the distal end of the cannula 32. Although three surgical tools are shown, more or fewer surgical tools may be implemented in alternative embodiments. The surgical tools 14a, 14b, 14c each may include a controllably extendable, rotatable, and bendable arm to which an end effector is coupled to by a wrist mechanism.

The imaging system 15 may include a stereoscopic pair of imaging sensors 51 (and/or a single binocular camera sensor) for three-dimensional imaging of the surgical site and an illuminating device 52 such as a light emitting diode (LED) or a fiber optics bundle carrying light from an external source, to enhance visibility of objects in the captured images. The imaging system 15 also has a controllably extendable, rotatable, and bendable arm 53 that facilitates at least insertion/retraction of the imaging system 15 along its longitudinal axis and pitch motion in order to achieve a sufficient elevation of the imaging system 15 "above" the surgical tools 14a, 14b, 14c so as to properly view them during a surgical procedure. Additional degrees of freedom, such as roll angular movement of the imaging system 15 about its insertion axis, may also be provided in order to facilitate additional positioning and orientation capabilities for the imaging system 15. For enhanced maneuverability, imaging system 15 may also be bendable such as the controllably bendable, rotatable, and extendable arms of the surgical tools 14a, 14b, 14c. Communication between the imaging system 15 and the cannula 32 is provided by one or more communication lanes that extend through a spatially restrictive structure (e.g. a shaft 35) and provide power, control, and data signaling for the imaging system 15.

Figure 2:
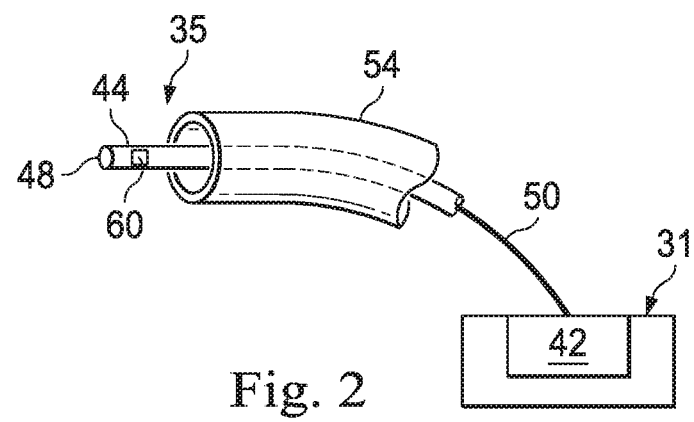
FIG. 2 is a representative perspective view of a teleoperated manipulating arm with an endoscopic imaging system, which can benefit from the current disclosure, installed on the manipulating arm, according to one or more embodiments.

FIG. 2 illustrates the distal end of a cannula 54 (e.g. cannula 32 or another cannula) and an instrument 44 (e.g. instruments 14a, 14b, 14c, 15). The instrument (or elongate member) 44 may be flexible and/or bendable along its elongated body or may include one or more localized flexible or bendable sections. One or more sensors 60 (e.g. image sensors, temperature sensors, pressure sensors, fluid flow sensors, etc.) positioned at a distal end 48 of an elongate member 44 which can communicate via a conductor 50 to a system interface 42 at a proximal end of the elongate member 44. The system interface 42 can be included in the carriage 31. The conductor 50 may be, for example, a wire or an optical fiber, and may be used to, for example, transmit power, control signals, and/or high-speed digital data. The system interface 42 can communicate with the control system 20 (e.g., via the carriage 31) to control, monitor, and power the sensors 60. Some sensors 60 (such as image sensors) can require increased communication bandwidth to the system interface 42, via communication lanes (or paths) that include the conductor 50. Communications lanes 68A, 68B, for example are described in later figures. A communication lane 68A or 68B can include at least a portion of the system interface 42, the conductor(s) 50, filtering circuitry, and one or more of the sensors 60. To increase bandwidth capabilities from the sensors 60 to the system interface 42, multiple communication lanes can be used. Increased data rates can be limited by the properties of the physical medium of the conductors 50 and by the number of conductors allowed through the spatially restrictive structure (e.g. shaft 35). As disclosed herein, the number of communication lanes (and their respective conductors 50) required to support communication between the sensors 60 and the control system 20 (via the interface 42, in this example), may be reduced by combining signals and power within a communication lane. The following discussion may be generally related to an electrical interface between the sensors 60 and the control system 20, via the conductors 50, and the interface 42. However, these principles can also be applied to communication lanes 68 that use optical waveguides instead of the conductors 50 for transmitting optical signals in both directions and powering the sensors 60 via optical power transmitted over the waveguides.

As way of example, an imaging system 15 will be discussed to describe the principles of the current disclosure. However, the current disclosure is not limited to imaging systems. Other sensors (e.g. temperature, pressure, fluid flow, etc.) used in other systems can also benefit from the principles of this disclosure. In an overview, the principles of the current disclosure may apply to any system that can benefit from a reduced number of electrical or optical conductors used to communicate power, control signals, and data signals through a spatially restrictive structure (such as the instrument 44).

Figure 3:
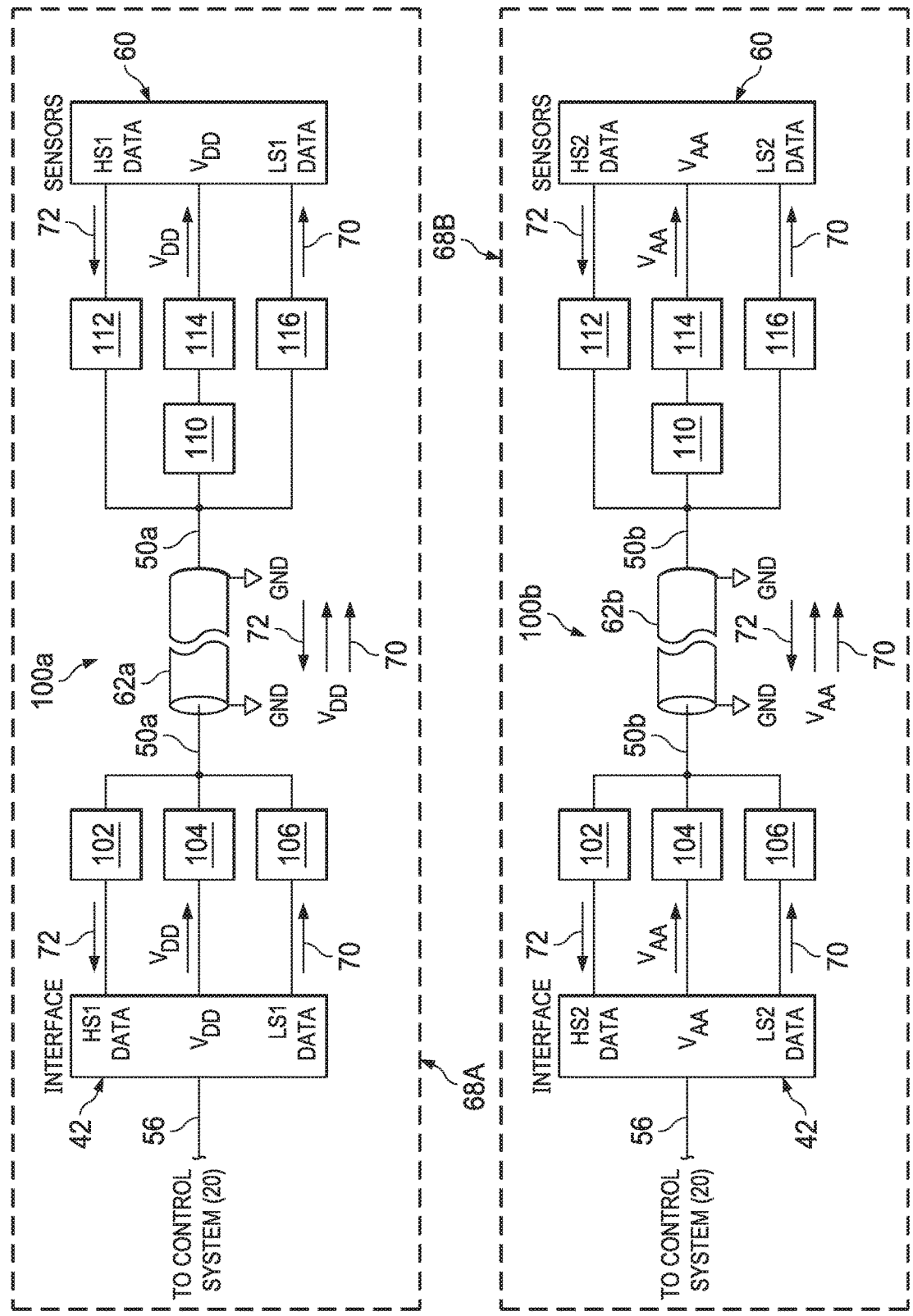
FIG. 3 is a representative schematic of two similar communication lanes that can interface sensors at a distal end of an elongate member with an interface at another end of the elongate member, according to one or more embodiments.

Referring to FIG. 3, schematic block diagrams are provided of two communication lanes 68A, 68B. The following discussion relates to the communication lane 68A, but is to be similarly applied to the communication lane 68B, since these communication lanes are intended to be duplicate circuits for this example, but carrying additional data and power signals. It should be understood that more or fewer communication lanes 68 can be utilized to provide various communication bandwidths between the sensors 60 and the control system 20. Also, multiple communication lanes 68 can be used that are not duplicates of each other.

The communication lane 68A can include a set of sensors 60 connected to an interface 42 via circuit modules and a transmission line 100a, which can include one or more conductors 50a. The transmission line 100a can be installed through a shaft 35 on the carriage 31, and can be referred to as an elongate member 44. The grounded shield 62a can be used to isolate the conductor 50a along the length of the transmission line 100a and can create a desired impedance (e.g. 50 ohms) for the transmission line 100a. The shield 62a is shown connected to a ground GND reference at each end of the transmission line 100a. However, only one end of the shield may be connected to the ground GND reference with the other end disconnected from the ground GND, in order to reduce or minimize potential ground loops when multiple communication lanes are used. At least one of the communication lanes may be connected at both ends of the transmission line 100a to the ground GND reference so the sensors 60 are supplied with a connection to the ground GND reference, or one or more of the conductors 50a may be used to provide the GND reference.

In one example of the type of signals that can be transmitted via the communication lane 68A, high-speed data HS1 can be transmitted from the sensors 60 to the interface 42 via the transmission line 100a, low-speed data LS1 can be transmitted from the interface 42 to the sensors 60 via the transmission line 100a, and power signals can be transmitted from the interface 42 to the sensors via the transmission line 100a. The concurrent transmission of these signals and power can be performed via time-domain multiplexing (TDM) or frequency domain multiplexing (FDM). In either configuration (TDM or FDM), the power signals can be transmitted by the transmission line 100 at a very-low frequency spectrum (e.g. <1 KHz for electrical conductors 50, but other frequencies can be utilized if optical waveguides are used) and can be transmitted simultaneously with either one or both of the high-speed data HS1 and the low-speed data LS1. However, it is intended that the high-speed data HS1 and the low-speed data LS1 do not occupy the same or overlapping frequency spectrums and be transmitted at the same time over the transmission line 100a. The TDM and FDM configurations usually perform one or the other. It should be understood, however, that the data HS1, LS1 can possibly occupy the same frequency spectrum and be transmitted at the same time over the transmission line 100a, but the additional circuitry needed to implement this configuration can further limit the number of communication lanes 68 that can be installed in the restrictive space of the shaft 35. The TDM and FDM configurations will now be discussed with reference to the circuitry shown in FIG. 3. It should also be understood that additional and/or alternative circuitry can be used to facilitate transmission of different types of signals, such as bi-directional signals for either or both of the high-speed data HS1 and low-speed data LS1.

In the TDM configuration, the high-speed data HS1 and low-speed data LS1 (arrows 72, 70, respectively) can be transmitted through the transmission line 100a at different time periods. Switching circuitry can alternately switch the high-speed data HS1 and the low-speed data LS1 onto the transmission line 100a so the two data types are transmitted through the transmission line 100a at different time periods. In one time period, the switching circuits can be selected to transmit the high-speed data HS1 into one end of the transmission line 100a, with the switching circuits at the other end being selected to direct the transmitted data to a high-speed data HS1 receiver. In another time period, the switching circuits can be selected to transmit the low-speed data LS1 into one end of the transmission line 100a, with the switching circuits at the other end being selected to direct the transmitted data to a low-speed data LS1 receiver. Alternating between the high-speed data HS1 and the low-speed data LS1 can provide continuous communication for these data types through the transmission line 100, where continuous communication may include time period gaps in each data type as the other data type is being transmitted, but communication for these data types can be maintained.

The data types can be transmitted through the transmission line 100a in either direction, as long as there is a transmitter at one end of the transmission line 100a and a receiver at the other end. The receivers and transmitters can be bi-directional transceivers that support the transmission of the data types in both directions. It can be beneficial for the high-speed data HS1 to be transmitted from the sensors 60, through the transmission line 100a, and received at the interface 42 for communicating the high-speed data HS1 (such as video data) to the computer system 20. The low-speed data LS1 can be used to transmit control data from the computer system 20, via the interface 42, through the transmission line 100a, and to the sensors 60 for controlling the sensors. Control signals, such as feedback of sensors states, can be communicated from the sensors 60 to the control system via the high-speed data HS1 signal transmission and/or through a low-speed data LS1 communication from the sensors 60 to the control system 20 (via the interface 42) over a bi-directional transmission line 100a, or over a uni-directional transmission line 100a at a different frequency spectrum or at a different time period from the other data types. It should be understood that it is not a requirement that the high-speed data HS1 and low-speed data LS1 be used in this manner. These are merely examples of how the data types can be used. It should also be understood that additional data types can be transmitted over the transmission line 100a, if additional time periods are available while maintaining a necessary bandwidth for each data type.

Figure 4:
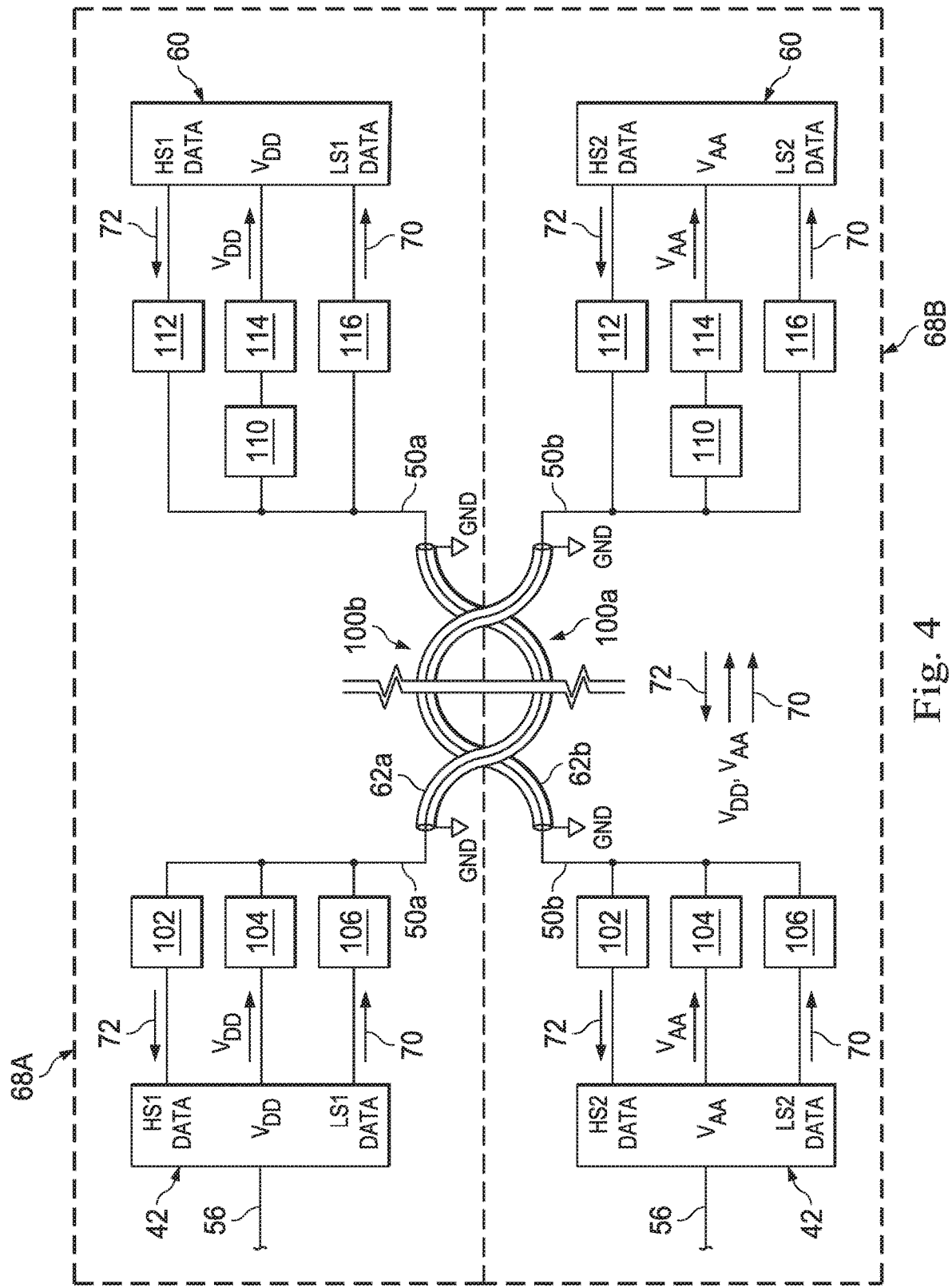
FIG. 4 is another representative schematic of two similar communication lanes that can interface sensors at a distal end of an elongate member with an interface at another end of the elongate member, according to one or more embodiments.

Referring again to FIG. 3, a cable 56 can connect the control system 20 to the interface 42. The cable 56 can include multiple conductors contained in one or more cables that interconnect the interface 42 with the control system. The interface 42 can be connected to the transmission line 100a via the circuit modules 102, 104, 106. Circuit modules 102 and 106 can include the switching circuitry for selectively connecting high-speed data HS1 and low-speed data LS1 paths (see arrows 72, 70, respectively) to a proximal end of the transmission line 100a, where the proximal end is the end of the transmission line 100a that is closest to the proximal end 46 of the elongate member 44. The circuit modules 102, 104, 106 can be connected together at the proximal end of the transmission line 100a that is also the proximal end of conductor 50a, with each one of the circuit modules 102, 104, 106 connected independently to the interface 42, as shown in FIGS. 3 and 4. The circuit modules 110, 112, 116 can be connected together at a distal end of the transmission line 100a that is also the distal end of conductor 50a (i.e. the end closest to the distal end 48 of the elongate member 44), with the circuit modules 112, 116 connected independently to the sensors 60. The circuit module 110 can be connected to the sensors 60 via a circuit module 114. The circuit modules in FIGS. 3 and 4 can be incorporated into the respective interface 42 or sensors 60, or one or more of the circuit modules can be separate from the interface 42 or sensors 60. The circuit modules 112 and 116 can include the switching circuitry for selectively connecting high-speed data HS1 (arrow 72) and low-speed data LS1 (arrow 70) paths to the distal end of the transmission line 100a. Therefore, when the switching circuits in the circuit modules 102 and 112 are switched to connect the high-speed data HS1 (arrow 72) to the transmission line 100a, the circuit modules 106 and 116 can be used to switch the low-speed data LS1 (arrow 70) off of the transmission line 100a, thereby preventing interference between the two data types in the transmission line 100a. The selective switching of the high-speed data HS1 (arrow 72) and the low-speed data LS1 (arrow 70) onto the transmission line 100a can allow for these two data types to occupy the transmission line 100a at different time periods.

The power supply voltage Vdd, which can be sourced from the interface 42, can be connected to the transmission line 100a via the circuit module 104 at the proximal end of the transmission line 100a and via the circuit modules 110 and 114 at the distal end of the transmission line 100a, and transmitted through the transmission line 100a to the sensors 60 as a power signal that supplies power Vdd to the sensors 60. Unlike the data types in the TDM configuration, the power signal can be applied to the transmission line 100a simultaneously with transmission of either one of the data types HS1, LS1. The circuit module 104 can be a filter circuit used to launch a power signal into the proximal end of the transmission line 100a, where the power signal occupies a very low-frequency band (0-1 KHz). The circuit module 110 can be a filter circuit used to receive the low-frequency power signal from the distal end of the transmission line 100a and present the power signal to the circuit module 114. The circuit module 114 can be a power regulator that receives the power signal Vdd and outputs the power voltage Vdd to the sensors 60 to power the sensors. This power signal may be needed to keep the sensors 60 powered and functioning properly.

Additional power signals can be supplied to the sensors 60 from the interface 42 via one or more additional transmission lines 100, with at least one additional transmission line 100b shown in the second communication lane 68B of FIG. 3. The communication lane 68B can provide a power voltage Vaa as a separate power signal over the conductor 50*b* of the transmission line 100*b*, with the circuit modules 104, 110, and 114 performing similar functions for the communication lane 68B as the circuit modules 104, 110, and 114 in the communication lane 68A, thereby supplying the power voltage Vaa to the sensors 60. Therefore, at least one power signal can be supplied over each transmission line 100*a*, 100*b*, etc. that is coupled between interface(s) 42 and sensors 60. The bandwidth of the high-speed data HS1 and the low-speed data LS1 (arrows 72, 70, respectively) between the interface(s) 42 and the sensors 60 can be increased by providing multiple communication lanes, such as the lane 68B, as well as providing additional power voltages to the sensors 60, such as power voltage Vaa.

In the FDM configuration, the high-speed data HS1 and low-speed data LS1 (arrows 72, 70, respectively) can be modulated and/or encoded onto the transmission line 100*a* such that they occupy separate frequency spectrums, and can be launched onto the transmission line 100*a* simultaneously as well as in separate directions, if desired. Signals transmitted over one frequency spectrum generally do not interfere with signals transmitted over the other frequency spectrum when the FDM configuration is used. Since data types HS1, LS1, and power can travel simultaneously over the transmission line 100*a*, the available bandwidth over the transmission line 100*a* can be optimally utilized. Coders (i.e. encoders and decoders) in the sensors 60 and the interface 42 can be used to control bandwidth used by the high-speed data HS1 (arrow 72) and the low-speed data LS1 (arrow 70) types. Frequency-selective filters can be used to direct the two data types to the correct receivers connected to the transmission line 100*a*. It should be understood that additional data types can be transmitted over the transmission line 100*a*, if additional frequency spectrums are available through the transmission line 100*a*.

Referring again to FIG. 3, the circuit modules 106, 102, 112, 116 can be used to encode and decode the data types HS1 and LS1 onto the transmission line 100*a*, such that the data types HS1, LS1 occupy different frequency spectrums. For example, the circuit module 112 can encode the high-speed data HS1 to occupy a high-frequency spectrum (e.g. 100 MHz to 6.25 GHz) and transmit the HS1 data to the transmission line 100*a*. The circuit module 102 can receive data transmitted via the transmission line 100*a*, filter the high-speed data HS1 from the transmitted data by applying a high-pass filter to the transmitted data and decode the high-speed data HS1 from the filtered data. The circuit module 102 can then transmit the high-speed data HS1 to the interface 42, which can transfer the data HS1 to the control system 20.

The control system 20 can transmit command and control data to the circuit module 106, via the interface 42 (arrow 70). The circuit module 106 can encode the low-speed data LS1 to occupy a low-frequency spectrum (e.g. 5 to 10 Mbps) and transmit the LS1 data to the transmission line 100*a*. The circuit module 116 can receive data transmitted via the transmission line 100*a*, filter the low-speed data LS1 from the transmitted data by applying a low-pass filter to the transmitted data and decode the low-speed data LS1 from the filtered data. The circuit module 116 can then transmit the low-speed data LS1 (arrow 70) to the sensors 60 for providing command and control data to the sensors. The encoding/decoding circuitry (e.g. Manchester encoding, 8b/10b encoding, etc.) can be included in the respective interface 42 and/or sensors 60, if desired, with filtering circuitry included in the circuit modules 102, 106, 112, 116.

Since the high-speed data HS1 and low-speed data LS1, can occupy different frequency spectrums (e.g. high frequency and low frequency spectrums, respectively), they can be transmitted through the transmission line 100*a* at the same time and in the same or different directions. This allows the transmission line 100*a* to provide an increased bandwidth for the high-speed data HS1 and the low-speed data LS1 compared to a TDM configuration. However, more circuitry can be needed for the FDM configuration compared to the TDM configuration, since the TDM configuration may not require encoding/decoding.

The power transmission to the sensors 60 for the FDM configuration is very similar to the power transmission of power voltages Vdd, Vaa described above for the TDM configuration. The power voltage Vdd, Vaa can be transmitted through the transmission line 100*a* along with two data types (HS1, LS1), with the power signals Vdd, Vaa transmitted over the transmission lines 100*a*, 100*b* in a very low-frequency band (0 to 1 KHz).

It should be understood that in some embodiments the functions of the circuit modules 106, 102 (and similarly modules 112, 116) can be combined into a single device, which can take the low-speed data LS1 (arrow 70) from the LS1 DATA output of the interface 42 and couple it onto the transmission line 100*a*, while simultaneously taking energy coming from the transmission line 100*a* (arrow 72) and direct it to the HS1 DATA input of the interface 42. The single device can be referred to as an RF circulator. The single device can receive energy in one port and direct the energy to an adjacent next port. At the other end of the transmission line 100*a*, a similar device can combine the functions of modules 112, 116 and direct energy from the transmission line 100*a* to the LS1 DATA input of the sensors 60 (arrow 70) and direct energy from the HS1 DATA port from the sensors 60 onto the transmission line 100*a* (arrow 72). The transmission of the power signals Vdd and Vaa can be transmitted across the transmission lines as in the other embodiments, without the power signals going through the single devices.

Referring to FIG. 4, schematic block diagrams are provided for the two communication lanes 68A, 68B. The example communication lanes 68A, 68B in FIG. 4 can be very similar to the communication lanes 68A, 68B shown in FIG. 3, except that the transmission lines 100*a*, 100*b* are helically wrapped around each other. This helical wrapping can help minimize or at least reduce stresses on the conductors 50*a*, 50*b* while the sensors 60 are articulated about at the distal end of the elongate member 44. Due to the helical wrapping, stresses on the conductors 50*a*, 50*b* and the shields 62*a*, 62*b* can be minimized by evening any bending stresses between the communication lanes 68A, 68B. The grounded shields 62*a*, 62*b* can isolate the conductors 50*a*, 50*b*, respectively, and can help control the impedance of the transmission lines 100*a*, 100*b*, respectively, by providing a substantially uniform reference plane for the conductors 50*a*, 50*b*.

The helical wrapping of the pair of conductors 50*a*, 50*b* or pair of transmission lines 100*a*, 100*b* can help improve cable flex life because the cable construction passing through the wrist is more symmetric, consisting of a pair of identical conductors, which can individually be made to flex repeatedly minimizing failures while still using current cable constructions. The pair may be balanced for a particular wrist design by twisting the transmission lines 100*a*, 100*b* together, so the net length change through the wrist is zero for each direction of articulation. This can reduce the asymmetric forces on the members and therefore a tendency to bunch and fail at resulting isolated points of high stress. The helical wrapping of the pair can also help improve the packaging of the connections of the conductors, because methods to terminate the coax cables with a single inner conductor are well known. Termination methods can also be developed specific to an application, such as the example applications in this disclosure. With two connections to make, and each connection being the same type of termination, additional design flexibility exists in allocating the scarce space at the back of the endoscope, which can be especially beneficial in articulating endoscopes.

Figure 5:
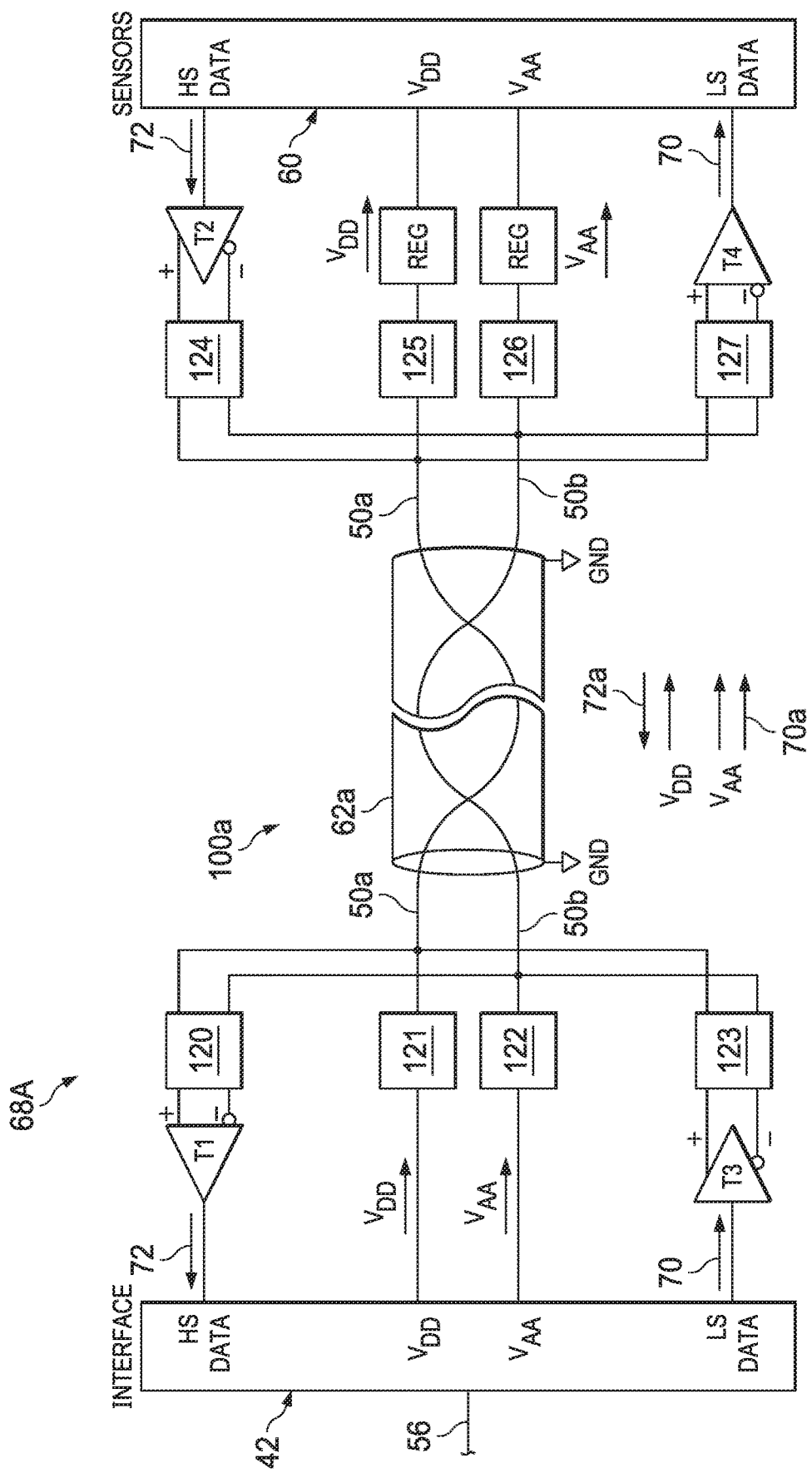
FIG. 5 is a representative schematic of a communication lane that can interface sensors at a distal end of an elongate member with an interface at another end of the elongate member, according to one or more embodiments.

Referring to FIG. 5, a schematic block diagram of another example of a communication lane 68A is provided. The communication lanes of FIGS. 3 and 4 are directed to single-ended circuitry. The circuitry in FIG. 5 is directed to a communication lane 68A that utilizes differential signal transmission over the transmission line 100a. Generally, differential signal transmissions are less susceptible to environmental noise than single-ended signal transmissions. As seen in the example communication lane 68A in FIG. 5, the transmission line 100a includes a set of conductors 50a, 50b that are helically wrapped around each other and the twisted set of conductors 50a, 50b can be isolated by a grounded shield 62a. This configuration can be referred to as a shielded twisted pair (STP) cable. One conductor 50a, can carry the positive signal of a differential signal being transmitted over the transmission line 100a, while the other conductor 50b of the STP cable can carry the negative signal of the differential signal being transmitted. The communication lane 68A can contain circuitry that converts single-ended data signals to differential data signals for transmission over the transmission line 100a. For example, the high-speed data HS1 can be output from the sensors 60 as single-ended signals 72 and converted to differential signals 72a by the transceiver T2. The output of the transceiver T2 is the positive and negative differential representations of the single-ended data signals 72. The circuit module 124 can be used to switch the differential high-speed data HS1 (signal 72a) onto the transmission line 100a at the appropriate time (such as in a TDM configuration) and/or it can include filtering and/or encoding circuitry for when the differential high-speed data HS1 occupies a high frequency spectrum (such as in a FDM configuration). At the other end of the transmission line 100a a circuit module 120 can detect the differential high-speed data HS1 (signal 72a) on the transmission line 100a and direct the differential high-speed data HS1 (signal 72a) to the transceiver T1, which can convert the differential high-speed data HS1 (signal 72a) to single-ended high-speed data HS1 (signal 72) that can be received at the interface 42 and transmitted on to the control system 20.

Additionally, the low-speed data LS1 can be output from the interface 42 as single-ended signals 70 and converted to differential signals 70a by the transceiver T3. The output of the transceiver T3 is the positive and negative differential representations of the single-ended data signals 70. The circuit module 123 can be used to switch the differential low-speed data LS1 (signal 70a) onto the transmission line 100a at the appropriate time (such as in a TDM configuration) and/or it can include filtering and/or encoding circuitry for when the differential low-speed data LS1 occupies a low frequency spectrum (such as in a FDM configuration). At the other end of the transmission line 100a a circuit module 127 can detect the differential low-speed data LS1 (signal 70a) on the transmission line 100a and direct the differential low-speed data LS1 (signal 70a) to the transceiver T4, which can convert the differential low-speed data LS1 (signal 70a) to single-ended low-speed data LS1 (signal 70) that can be received at the sensors 60 for possible command and control of the sensors 60.

Since the STP cable in FIG. 5 contains two conductors 50a, 50b, then two power signals can be carried by the communication lane 68A from the interface 42 to the sensors 60. A first power supply signal Vdd can be coupled to the conductor 50a by circuit module 121, while a second power supply signal Vaa can be coupled to the conductor 50b by circuit module 122. The power signals Vdd, Vaa can then be transmitted over the transmission line 100a to circuit modules 125, 126, respectively, which can direct the power signals Vdd, Vaa to respective regulators REG that can reform the desired power supply voltages Vdd, Vaa to be used for powering one or more sensors 60. As can be seen, similar to the single-ended signals in FIGS. 3 and 4, the differential signals in FIG. 5 can support transmission of the high-speed data HS1, the low-speed data LS1, and the power supply signals Vdd, Vaa over the same transmission line 100a for either TDM and FDM configurations.

Figure 6:
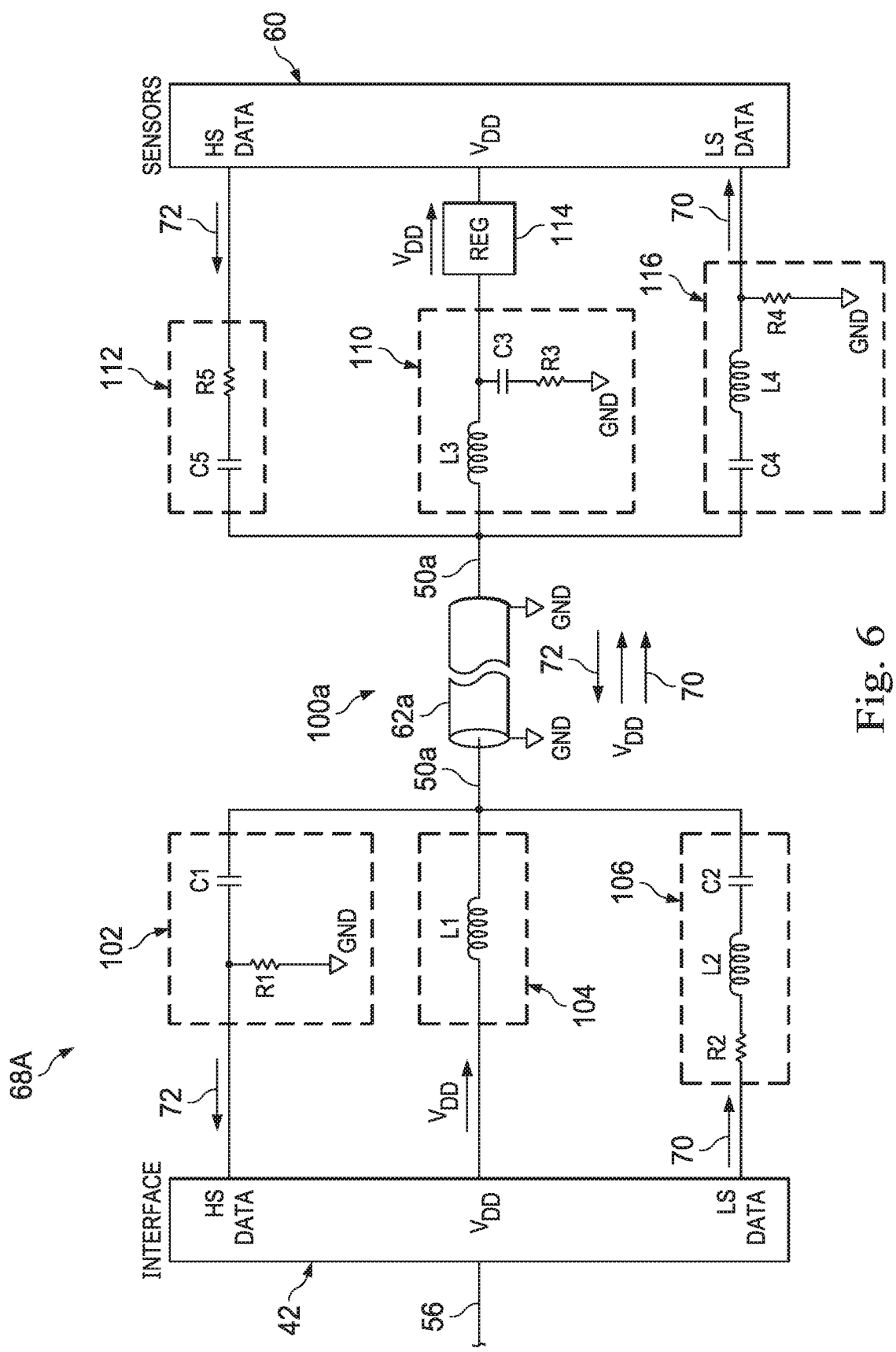
FIG. 6 is a representative detailed schematic of circuitry either one of the communication lanes of FIG. 3 that can interface sensors at a distal end of an elongate member with an interface at another end of the elongate member, according to one or more embodiments.

FIG. 6 is a representative circuit diagram of a communication lane 68A using single-ended signals for the high-speed data HS1 and the low-speed data LS1. FIG. 6 is similar to the schematic block diagram of the communication lane 68A of FIG. 3, with example circuitry components for each of the circuit modules. It should be understood that many other combinations of individual circuit components (such as resistors designated by Rx, capacitors designated by Cx, and inductors designated by Lx) can be used other than the example components shown in FIG. 6. The filtering functions may also be realized by utilizing active components such as amplifiers and switched-capacitor circuits. The components C5, R5 of the circuit module 112 can be used as shown to filter out low-frequency signals in the high-speed data HS1 (signal 72) that is transmitted from the sensors 60 to one end of the transmission line 100a. The components R1, C1 of the circuit module 102 can be used as shown to filter out low-frequency signals received from the transmission line 100a, thereby extracting the high-speed data HS1 (signal 72) from the signals transmitted over the transmission line 100a. Also different values of these components as well as more, fewer, and/or other components (e.g. switching circuitry) can be used. The components R2, L2, C2 of the circuit module 106 can be used as shown to filter out very low-frequency (e.g. 0-1 KHz) and high-frequency signals (e.g. 100 MHz to 20 GHz) in the low-speed data LS1 (signal 70) that is transmitted from the interface 42 to one end of the transmission line 100a. The components R4, L4, C4 of the circuit module 116 can be used as shown to filter out very low-frequency and high-frequency signals received from the transmission line 100a, thereby extracting the low-speed data LS1 (signal 70) from the signals transmitted over the transmission line 100a. Also, different values of these components as well as more, fewer, and/or other components (e.g. switching circuitry) can be used. Regarding the power signal Vdd, the component L1 of the circuit module 104 can be used to couple the voltage Vdd to the transmission line 100a at one end and the components R3, L3, C3 of circuit module 110 can be used to filter out the low-frequency (e.g. 10 KHz to 100 MHz) and high-frequency (e.g. 100 MHz to 20 GHz) from the signals transmitted over the transmission line 100a, thereby allowing the very-low frequency power signal Vdd to be extracted from the transmission line 100a and output from the circuit module 110 to the circuit module 114, which can be a regulator REG that can reform the power signal Vdd before outputting the power signal Vdd to the sensors 60. As stated above, the high-speed data HS1, the low-speed data LS1, and the very-low speed data (e.g. the power signal Vdd) can be transmitted simultaneously over the transmission line 100a in either direction, thereby reducing the amount of conductor connections at the sensors that can be required to power, control, and receive data from the sensors 60.

Figure 7:
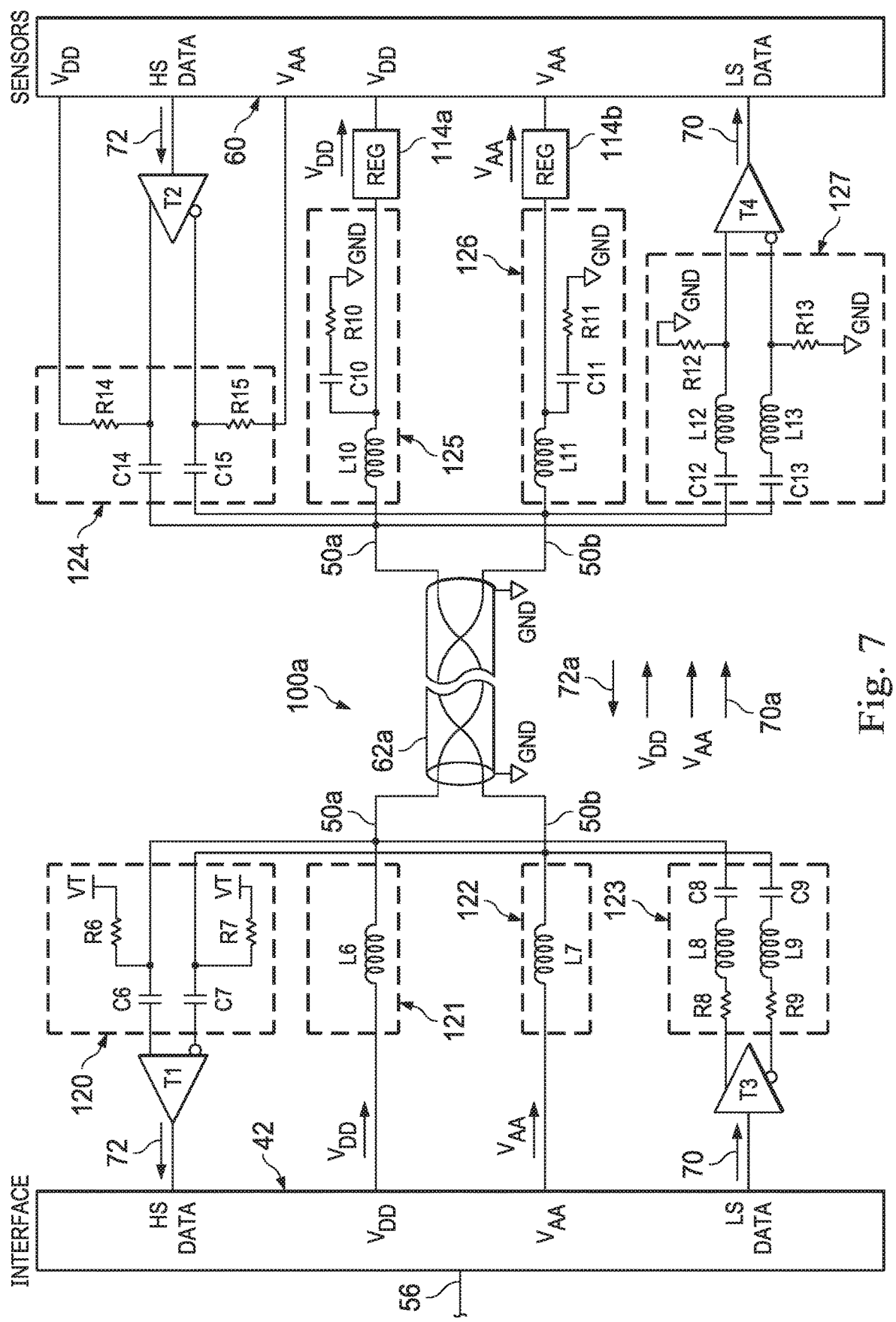
FIG. 7 is a representative detailed schematic of circuitry for the communication lane of FIG. 5 that can interface sensors at a distal end of an elongate member with an interface at another end of the elongate member, according to one or more embodiments.

FIG. 7 is a representative circuit diagram of a communication lane 68A using differential signals for the high-speed data HS1 and the low-speed data LS1. FIG. 7 is similar to the schematic block diagram of the communication lane 68A of FIG. 5, with example circuitry components for each of the circuit modules. It should be understood that many other combinations of individual circuit components (such as resistors designated by Rx, capacitors designated by Cx, and inductors designated by Lx) can be used other than the example components shown in FIG. 7. In this example, the high-speed data HS1 can be output from the sensors 50 to the transceiver T2, which can convert the single-ended high-speed data HS1 (signal 72) from the sensors 60 to differential high-speed data HS1 (signal 72a) that can be output to the circuit module 124. The components C14, R14 of the circuit module 124 can be used as shown to filter out low-frequency signals in a positive signal of the differential high-speed data HS1 (signal 72a), with components C15, R15 of the circuit module 124 used as shown to filter out low-frequency signals in a negative signal of the differential high-speed data HS1 (signal 72a). The circuit module 124 can couple the filtered (and possibly encoded) data (i.e. signal 72a) to an end of the transmission line 100a, which can transmit the signal 72a to the other end of the transmission line 100a. At the other end, a circuit module 120 can be used to extract the differential high-speed data HS1 from the other signals transmitted over the transmission line 100a. The components R14, R15 can be connected to power voltages Vdd, Vaa as shown to provide a desired biasing of the outputs of the transceiver T2.

The components R6, C6 of the circuit module 120 can be used as shown to filter out low-frequency signals received from the transmission line 100a in the positive signal of the transmission line 100a, thereby extracting the positive signal of the differential high-speed data HS1 (signal 72a) from the signals transmitted over the positive signal of the transmission line 100a. The components R7, C7 of the circuit module 120 can be used as shown to filter out low-frequency signals received from the transmission line 100a in the negative signal of the transmission line 100a, thereby extracting the negative signal of the differential high-speed data HS1 (signal 72) from the signals transmitted over the transmission line 100a. The resulting differential high-speed data HS1 (signal 72a) can be output from the circuit module 120 to the transceiver T1, which can convert the differential high-speed data HS1 to a single-ended high-speed data HS1 (signal 72) that can be sent to the control system 20 via the interface 42. The components R6, R7 can be connected to a reference voltage as shown for a desired biasing of the transceiver T1 inputs. Also, different values of these components, as well as more, fewer, and/or other components (e.g. switching circuitry), can be used.

Single-ended low-speed data LS1 (signal 70) can be output from the interface 42 to the transceiver T3, which can convert the single-ended low-speed data LS1 (signal 70) into a differential low-speed data LS1 (signal 70a) The components R8, L8, C8 of the circuit module 123 can be used as shown to filter out very low-frequency and high-frequency signals in the positive signal of the differential low-speed data LS1 (signal 70a) that is transmitted from the transceiver T3 to the circuit module 123. The components R9, L9, C9 of the circuit module 123 can be used as shown to filter out very low-frequency and high-frequency signals in the negative signal of the differential low-speed data LS1 (signal 70a) that is transmitted from the transceiver T3 to the circuit module 123. The circuit module 123 can then transmit the filtered differential low-speed data LS1 (signal 70a) to respective conductors 50a, 50b at one end of the transmission line 100a, which can transmit the differential low-speed data LS1 (signal 70a) to another end of the transmission line 100a.

The components R12, L12, C12 of circuit module 127 can be used as shown to filter out very low-frequency and high-frequency signals in the positive signal of the transmission line 100a, thereby extracting the positive signal of the differential low-speed data LS1 (signal 70a) from the signals transmitted by the transmission line 100a. The components R13, L13, C13 of circuit module 127 can be used as shown to filter out very low-frequency and high-frequency signals in the negative signal of the transmission line 100a, thereby extracting the negative signal of the differential low-speed data LS1 (signal 70a) from the signals transmitted by the transmission line 100a. The circuit module 127 can then transmit the differential low-speed data LS1 (signal 70a) to the transceiver T4, which can convert the differential low-speed data LS1 (signal 70a) to the single-ended low-speed data LS1 (signal 70) and output the low-speed data LS1 (signal 70) to the sensors, which can include command and control data for the sensors 60. The components R12, R13 can be connected to a reference ground as shown for desired biasing of the transceiver T4 inputs.

Regarding the power signals Vdd, Vaa the components L6, L7 of the circuit module 121 can be used to couple the voltages Vdd, Vaa to one end of the respective conductors 50a, 50b of the transmission line 100a and the components R10, L10, C10 and R11, L11, C11 of circuit module 125 can be used to filter out the low-frequency and high-frequency signals from the signals transmitted over the transmission line 100a, thereby allowing the very-low frequency power signals Vdd, Vaa to be extracted from the transmission line 100a and then output from the circuit module 125 to the circuit modules 114a, 114b, which can be regulators REG that can reform the power signals Vdd, Vaa before outputting the signals Vdd, Vaa to the sensors 60. As stated above, the differential high-speed data HS1, the differential low-speed data LS1, and the very-low speed data (e.g. the power signals Vdd, Vaa) can be transmitted simultaneously over the transmission line 100a in either direction, thereby reducing the amount of conductor connections at the sensors that can be required to power, control, and receive data from the sensors 60 using differential signal transmission.

One or more elements in embodiments of the invention may be implemented in software to execute on a processor of a computer system such as control processing system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

Any reference to surgical instruments and surgical methods is non-limiting as the instruments and methods described herein may be used for animals, human cadavers, animal cadavers, portions of human or animal anatomy, non-surgical diagnosis, industrial systems, and general robotic or teleoperational systems.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. An imaging system for imaging an anatomy of a patient, the system comprising:
    a processor;
    an interface;
    at least one imaging sensor;
    first and second conductors;
    a shaft with the interface positioned at a proximal end of the shaft and the imaging sensor positioned at a distal end of the shaft, wherein the first and second conductors extend through the shaft and electrically couple the imaging sensor to the processor via the interface,
    wherein the first conductor transmits control signals, power signals, and imaging sensor data signals between the imaging sensor and the processor, and wherein the second conductor transmits control signals, power signals, and imaging sensor data signals between the imaging sensor and the processor.

2. The system of claim 1, wherein the first and second conductors are helically twisted about each other along a length of the first and second conductors.

3. The system of claim 2, wherein the first conductor is coaxially positioned within a first shield material forming a first coax cable, and the second conductor is coaxially positioned within a second shield material forming a second coax cable.

4. The system of claim 2, wherein a shield material at least partially surrounds the first and second conductors along a length of the first and second conductors, forming a shielded twisted pair cable.

5. The system of claim 2, wherein the helical twist of the first and second conductors evenly distributes stresses between the first and second conductors that are routed through an articulating joint of an endoscope.

6. The system of claim 1, wherein the power is a DC voltage that powers the imaging sensor.

7. The system of claim 1, wherein the control signals comprise low-speed control signals transmitted from the interface to the imaging sensor at a low-frequency spectrum, and wherein the imaging sensor data signals comprise high-speed sensor data signals transmitted from the imaging sensor to the interface at a high-frequency spectrum.

8. The system of claim 7, wherein the low-speed control signals are encoded and shaped to occupy a low frequency band in a range of 3 Mbps to 15 Mbps, and wherein the high-speed sensor data signals are encoded and shaped to occupy a high frequency band in a range of 100 MHZ to 6.25 GHZ.

9. The system of claim 7, wherein the low-speed control signals are transmitted from the interface during a first allocated time period, and the high-speed sensor data signals are transmitted from the imaging sensor at a high-frequency during a second allocated time period.

10. The system of claim 9, wherein the first allocated time period does not overlap the second allocated time period.

11. The system of claim 1, wherein the at least one imaging sensor includes multiple imaging sensors, wherein the first and second conductors form a communication lane that transmits the control signals, power signals, and imaging sensor data signals between the imaging sensors and the processor, and wherein the system further comprises multiple communication lanes.

12. A teleoperational medical system comprising:
    a control system with one or more processors;
    a teleoperational manipulator arm; and
    an imaging system attached to the teleoperational manipulator arm, the imaging system comprising:
        imaging sensors that detect image data and transmit imaging sensor data signals to the control system;
        a camera interface that interfaces the imaging sensors to the control system;
        first and second conductors that electrically couple the control system to the imaging sensors via the camera interface; and
        an elongate member with the imaging sensors positioned at a distal end of the elongate member, and the camera interface positioned at a proximal end of the elongate member, with the first and second conductors positioned within the elongate member,
        wherein the first conductor transmits control signals and power signals from the control system to the imaging sensors via the camera interface, and wherein the second conductor transmits control signals and power signals from the control system to the imaging sensors via the camera interface, and
        wherein the first conductor transmits imaging sensor data signals from the imaging sensors to the control system via the camera interface, and wherein the second conductor transmits imaging sensor data signals from the imaging sensors to the control system via the camera interface.

13. The system of claim 12, wherein the power signals comprise a first voltage carried to the imaging sensors by the first conductor and a second voltage carried to the imaging sensors by the second conductor.

14. The system of claim 12, wherein the control signals are encoded and shaped to occupy a low frequency spectrum, and the imaging sensor data signals are encoded and shaped to occupy a high frequency spectrum.

15. The system of claim 12, wherein the power signals, the control signals, and the imaging sensor data signals are transmitted simultaneously by each of the first and second conductors.

16. The system of claim 12, wherein the control signals and the imaging sensor data signals are transmitted by the first and second conductors at separate time periods.

17. The system of claim 12, wherein the first and second conductors are surrounded by one or more grounded shields, which supplies ground to the imaging sensors.

18. The system of claim 12, wherein the first and second conductors are helically twisted about each other, and wherein the helical twist of the first and second conductors evenly distributes stresses between the first and second conductors that are routed through an articulating joint of an endoscope.

19. A method of imaging an anatomy of a patient, the method comprising:

transmitting a power signal to imaging sensors of an elongate member Via first and second conductors of the elongate member thereby powering the imaging sensors, wherein the elongate member is attached to a teleoperational manipulator arm of a teleoperational medical system, wherein the imaging sensors are positioned at a distal end of the elongate member, wherein the first and second conductors are positioned within a lumen of the elongate member, and wherein the first and second conductors electrically couple the imaging sensors to a camera interface of the elongate member, wherein the camera interface is positioned at a proximal end of the elongate member;

transmitting control signals to the imaging sensors from the camera interface via the first and second conductors;

transmitting imaging sensor data signals to the camera interface from the imaging sensors via the first and second conductors; and receiving the imaging sensor data signals at one or more controllers and displaying an image, based on the imaging sensor data signals, on a display device.

20. The method of claim 19, further comprising transmitting the control signals from the camera interface to the imaging sensors within a low-frequency spectrum while, at the same time, transmitting the imaging sensor data signals from the imaging sensors to the camera interface within a high-frequency spectrum.

* * * * *